(12) United States Patent
Weller et al.

(10) Patent No.: US 7,479,864 B2
(45) Date of Patent: Jan. 20, 2009

(54) TOTAL FLUID CONDUCTIVITY SENSOR SYSTEM AND METHOD

(76) Inventors: Thomas M. Weller, 505 Crystal Grove Blvd., Lutz, FL (US) 33548; David P. Fries, 755 19th Ave. North, St. Petersburg, FL (US) 33704; Saravana P. Natarajan, 14240 N. 42nd St., #3701, Tampa, FL (US) 33620

( * ) Notice: Subject to any disclaimer, the term of this patent is extended or adjusted under 35 U.S.C. 154(b) by 7 days.

(21) Appl. No.: 11/425,231

(22) Filed: Jun. 20, 2006

(65) Prior Publication Data
US 2007/0008060 A1 Jan. 11, 2007

Related U.S. Application Data

(60) Provisional application No. 60/595,267, filed on Jun. 20, 2005.

(51) Int. Cl.
*H01F 5/00* (2006.01)
*H03K 9/06* (2006.01)
*H03D 1/00* (2006.01)

(52) U.S. Cl. .................. 336/200; 336/223; 336/229
(58) Field of Classification Search ............ 336/200, 336/223, 229; 327/50–52, 46–47
See application file for complete search history.

(56) References Cited

U.S. PATENT DOCUMENTS

| | | | |
|---|---|---|---|
| 4,352,288 A | 10/1982 | Paap et al. | |
| 6,600,404 B1 * | 7/2003 | Kajino | 336/200 |
| 6,975,199 B2 * | 12/2005 | Long et al. | 336/200 |
| 7,225,081 B2 * | 5/2007 | Kolosov et al. | 702/25 |
| 7,253,711 B2 * | 8/2007 | Pleskach et al. | 336/200 |
| 2005/0072217 A1 * | 4/2005 | Discenzo | 73/53.05 |

* cited by examiner

*Primary Examiner*—Anh T Mai
(74) *Attorney, Agent, or Firm*—Molly Sauter; Smith & Hopen, P.A.

(57) ABSTRACT

The present invention provides an apparatus and method for measuring the conductivity of a fluid employing the differential radio frequency phase detection between two embedded toroidal coils.

13 Claims, 14 Drawing Sheets

Fig. 7

| Design | Core Shape | No. Turns | Turn Length (mm) | Coil Area (mils²) | Configuration |
|---|---|---|---|---|---|
| SQ 8 | Square | 8 | 2 | 430x430 | 1- Port |
| SQ 12 | Square | 12 | 2 | 450X430 | 1- Port |
| SQ 20 | Square | 20 | 2 | 380X380 | 1- Port |
| SQ 1MM | Square | 12 | 1 | 360X350 | 1 and 2- Port |
| SQ 2MM | Square | 12 | 2 | 450X430 | 1 and 2- Port |
| SQ 3MM | Square | 12 | 3 | 520X510 | 1 and 2- Port |
| CIR 1MM | Circular | 10 | 1 | 66 | 1 and 2- Port |
| CIR 2MM | Circular | 10 | 2 | 81 | 1 and 2- Port |
| CIR 3MM | Circular | 10 | 3 | 140 | 1 and 2- Port |

Fig. 11

| DESIGN | L1 (nH) | ESR @ 200 MHz (Ω) | L2 (nH) | C1 (pF) | L3 (nH) | R1 (Ω) | C2 (pF) | C3 (pF) |
|---|---|---|---|---|---|---|---|---|
| SQ 8 TURNS | 1.50 | 0.97 | 21.01 | 1.44 | 1.49 | 0.42 | 0.03 | 4.57 |
| SQ 20 TURNS | 1.50 | 2.25 | 23.45 | 3.07 | 1.49 | 0.42 | 0.01 | 6.17 |
| SQ 1 MM | 1.50 | 0.90 | 17.09 | 1.47 | 1.49 | 0.42 | 0.34 | 5.46 |
| SQ 2 MM | 1.50 | 1.43 | 21.28 | 2.19 | 1.49 | 0.42 | 0.04 | 5.56 |
| SQ 3 MM | 1.50 | 2.86 | 25.74 | 2.46 | 1.49 | 0.42 | 0.03 | 6.67 |
| CIR 1 MM | 2.66 | 0.64 | 10.95 | 2.27 | 0.84 | 0.62 | ~0 | 6.14 |
| CIR 2 MM | 2.66 | 0.76 | 12.55 | 2.82 | 0.84 | 0.62 | ~0 | 7.72 |
| CIR 3 MM | 2.66 | 0.93 | 14.45 | 3.48 | 0.84 | 0.62 | ~0 | 11.64 |

Fig. 13

| DESIGN | SQ 8 | SQ 20 | SQ 1MM | SQ 2MM | SQ 3MM | CIR 1MM | CIR 2MM | CIR 3MM |
|---|---|---|---|---|---|---|---|---|
| Q Factor | 38 | 24 | 38 | 32 | 25 | 37 | 34 | 32 |
| Inductance(nH) @ 320 MHz | 32.42 | 56.23 | 27.47 | 37.26 | 50.45 | 18.03 | 20.94 | 27.43 |

TOTAL FLUID CONDUCTIVITY SENSOR SYSTEM AND METHOD

CROSS REFERENCE TO RELATED APPLICATIONS

This application claims priority to U.S. Provisional Patent Application 60/595,267, entitled, "Contact-less Fluid Conductivity Sensor Based on Radio Frequency Detection", filed Jun. 20, 2005.

STATEMENT OF GOVERNMENT INTEREST

This invention was made with Government support under Grant No. N00014-98-1-0848 awarded by the Office of Naval Research. The Government has certain rights in the invention.

BACKGROUND OF THE INVENTION

Harsh conditions make environmental monitoring a very challenging task. Sensors deployed for environmental monitoring must adhere to stringent quality requirements to ensure reliable data output. The ocean is an example of an environment in which salinity, temperature and pressure conditions result in a corrosive medium, making the task of environmental monitoring increasingly difficult.

Conductivity, temperature and depth (CTD) data of the ocean are important parameters for oceanographic research applications and are used to determine salinity of the ocean water. Conventional methods of measuring conductivity known in the art involve the immersion of two metal electrodes in a fluid whose conductivity is to be measured. A known current is then applied to one of the immersed electrodes and the resulting voltage is measured. The resistive loss as the current passes through the fluid is measured and converted to the corresponding conductivity reading.

One of the main problems associated with this prior art method is that corrosion and fouling of the metal electrodes in contact with the fluid commonly occurs. In an effort to eliminate the corrosion and fouling problems associated with this method, inductive type conductivity sensors have been introduced to the art. With this method, insulated toroidal coils are used to inductively couple an alternating signal through the fluid. The first coil is connected to a frequency oscillator, which induces a magnetic field within the coil. This field couples through the fluid and induces a current in the second coil. The voltage measured at the second coil is compared against a reference value to determine the voltage drop through the fluid. This value is then used to calculate the fluid conductivity as in the conventional design. The toroidal type design which employs insulated coils overcomes the problem of fouling, making it useful for corrosive environments like sea water.

Additionally, toroidal inductors are used in a number of RF (radio frequency) applications where good magnetic shielding is desirable. Conventional toroids, using a ferrite core, are also preferred in circuits that need high power handling capability, inductance and Q factor. The Q factor, or quality factor, of an inductor is the ratio of its inductance to its resistance at a given frequency, and is a measure of its efficiency. The higher the Q factor of the inductor, the closer it approaches the behavior of an ideal, lossless, inductor. Furthermore, the low stray-field intensity of toroidal inductors allows them to be placed in close proximity to other circuitry with low levels of parasitic cross-talk. The primary performance limitation of a ferrite core toroid is the loss due to the induction of eddy current. The loss due to eddy current can be reduced by proper selection of the core material, shape and turn diameter.

Miniaturization of electronic circuits is a goal in virtually every field, not only to achieve compactness in mechanical packaging, but also to decrease the cost of manufacture of the circuits. Many digital and analog circuits, including complex microprocessors and operational amplifiers, have been successfully implemented in silicon based integrated circuits (ICs). These circuits typically include active devices such as bipolar transistors and field effect transistors (FETs), diodes of various types, and passive devices such as resistors and capacitors.

One area that remains a challenge to miniaturize are radio frequency (RF) circuits, such as those used in cellular telephones, wireless modems, and other types of communication equipment. The problem is the difficulty in producing a good inductor in silicon technologies that is suitable for RF applications. Attempts to integrate inductors into silicon technologies have yielded either inductor Q values less than five or required special metallization layers such as gold.

It is well known that the direct current (DC) resistance of a metal line that forms a spiral inductor is a major contributor to the inductor Q degradation. One way to reduce this effect is to use wide metal line-widths, however, this increases the inductor area and the parasitic capacitance associated with the structure. The larger inductor area limits the miniaturization that can be achieved, and the parasitic capacitance associated with the larger area decreases the self-resonance frequency of the inductor, thereby limiting its useful frequency range. Also, since the Q is directly proportional to frequency and inversely proportional to the series loss of the inductor, the metal line widths cannot be chosen arbitrarily large.

There exists a need in the art for a miniaturized corrosion resistant conductivity sensor that can be easily packaged and fitted to a buoy and deployed in underwater applications and that has low power consumption.

SUMMARY OF INVENTION

The present invention is a toroidal inductive sensor for measuring the conductivity of a fluid using radio frequency techniques.

In a particular embodiment, the fluid conductivity sensor in accordance with the present invention includes a first toroidal coil embedded in a printed circuit board and a second toroidal coil embedded in a printed circuit board. The first coil is then positioned in close proximity to the second coil to establish a toroidal inductor having a core of dielectric material to measure the conductivity of the fluid between the coils when they are immersed in the fluid. A radio frequency phase detection circuit is then coupled to the toroidal inductor and used to measure the conductivity of the fluid.

The toroidal coils are embedded in the printed circuit board using conventional techniques for two-layer printed circuit board fabrication. As such, the coils in accordance with the present invention include a ground plane layer, a first dielectric substrate layer positioned adjacent to the ground plane layer, a first plurality of microstrip conductive elements positioned on the first dielectric substrate layer, a second dielectric substrate layer positioned to overly the first dielectric substrate layer and the first plurality of conductive elements, a second plurality of microstrip conductive elements positioned on the second dielectric substrate layer and a plurality of vias positioned to provide electric connection between the first plurality of conductive elements and the second plurality of conductive elements to establish a toroidal coil within the substrate layers of the printed circuit board.

In a specific embodiment, the dielectric substrate layers are composed of FR4. However, other materials known in the art for the fabrication of printed circuit boards are within the scope of the present invention.

In a specific embodiment, the first conductive elements and the second conductive elements are gold metallized, thereby providing low series resistance and high resistance to corrosion in the fluid.

The radio frequency phase detection circuit use to measure the conductivity of the fluid includes a voltage controlled oscillator tuned to output a radio frequency signal, a coupler coupled to the voltage controlled oscillator to generate a reference signal and an output signal from the radio frequency signal, the output signal of the coupler received as an input signal to the first toroidal coil, an amplifier to receive an output signal from the second toroidal coil in response to the input signal to the first toroidal coil and a frequency mixer to receive the reference signal from the coupler and the output signal from the second toroidal coil, and to output a phase difference signal representing the difference between the reference signal from the coupler and the output signal from the toroidal coil.

Additionally, the radio frequency phase detection circuit may further include a filter circuit coupled to the output of the frequency mixer to remove any harmonics from the output signal of the frequency mixer.

A phase shifter may also be included in the radio frequency phase detection circuit to modify the output voltage from the second toroidal coil for calibration and initial adjustment purposes.

In a particular embodiment, a thermistor is mounted to the toroidal coil to monitor the temperature of the fluid.

In accordance with the present invention, a method for measuring the conductivity of a fluid is provided, the method includes placing a first toroidal coil embedded in a printed circuit board and a second toroidal coil within a fluid to be measured, the first coil positioned in close proximity to the second coil to establish a toroidal inductor having a core of dielectric material and measuring the conductivity of the fluid using a radio frequency phase detection circuit coupled to the toroidal inductor.

In measuring the conductivity of the fluid, the present invention includes the steps of establishing a radio frequency signal, splitting the radio frequency signal to generate a reference signal and an output signal from the radio frequency signal, providing the output signal as an input signal to the first toroidal coil, establishing an output signal from the second toroidal coil in response to the input to the first toroidal coil, amplifying the output signal from the second toroidal coil and measuring the phase difference between the amplified output signal from the second toroidal coil and the reference signal, the phase difference representative of the conductivity of the fluid.

In accordance with a particular embodiment of the present invention, a method for detecting the conductivity of the fluid includes the steps of providing an input voltage to one of the two insulated coils, establishing an alternating signal coupled between the two coils, detecting a phase change between the alternating signal that couples between the two closely held coils inside the fluid, converting the phase change into an output voltage, and calculating the conductivity based on the output voltage and a reference voltage. In a particular embodiment, the sensing circuitry, which provides the input and converts the phase change into an output voltage is also assembled and integrated with the sensor.

As such, the present invention provides an embedded sensor that can be easily packaged, fitted to a buoy and deployed in underwater applications. The toroidal type sensors in accordance with the present invention are not prone to corrosion and fouling. The embedded design of the coils and sensing circuitry allow the sensor to be easily integrated with other systems. An integrated thermistor mounted on the coil allows for in-situ temperature monitoring and can be used for compensation. The design of the conductivity sensor in accordance with the present invention allows for low power consumption.

BRIEF DESCRIPTION OF THE DRAWINGS

For a fuller understanding of the invention, reference should be made to the following detailed description, taken in connection with the accompanying drawings, in which:

FIG. 7 is table illustrating a variety of toroidal coil designs within the scope of the present invention.

FIG. 11 is a table illustrating the component values extracted from the equivalent circuit model data.

FIG. 13 is a table illustrating the measured Q-factor values for a variety of toroidal designs.

DETAILED DESCRIPTION OF THE PREFERRED EMBODIMENT

Figure 1:
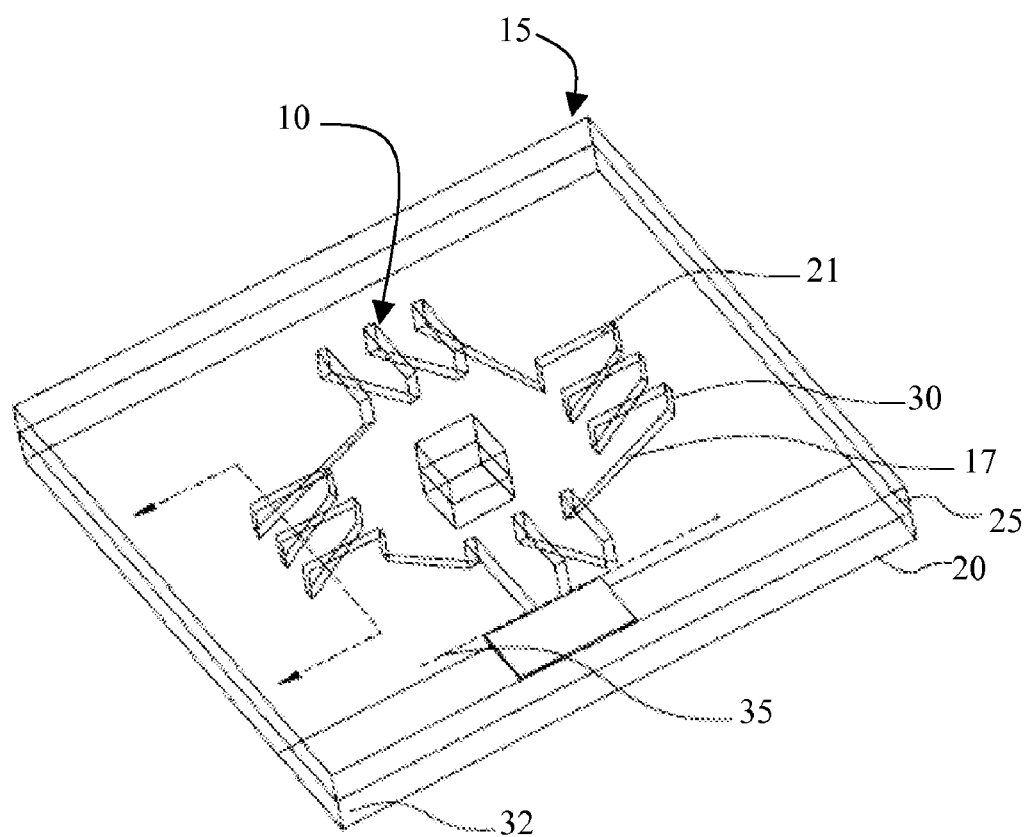
FIG. 1 is a three-dimensional diagrammatic view illustrating the embedded toroidal coil of the conductivity sensor in accordance with the present invention.

With reference to FIG. 1, each of the toroidal coils 10 in accordance with the present invention are embedded in a printed circuit board 15. The printed circuit board has a ground plane 32 and the coil windings are laid out as microstrip lines 17 on a first substrate 20 and microstrip lines 21 on a second substrate 25 and interconnections are formed to the backside of the board using plated thru vias 30. The pair of coils are then held in close proximity to each other inside the fluid. As such, a toroidal coil is formed having a core of dielectric material. In a particular embodiment, 10 mil line widths and 12 mil minimum via hole dimensions are used to suit the processing parameters typical of printed circuit board manufacturers. The toroidal coil is then connected to a 50 ohm feed line 35 for performing the conductivity measurements utilizing a radio frequency phase detector. In a specific embodiment the printed circuit board layers are 31-mil thick FR4 layers.

Figure 2:
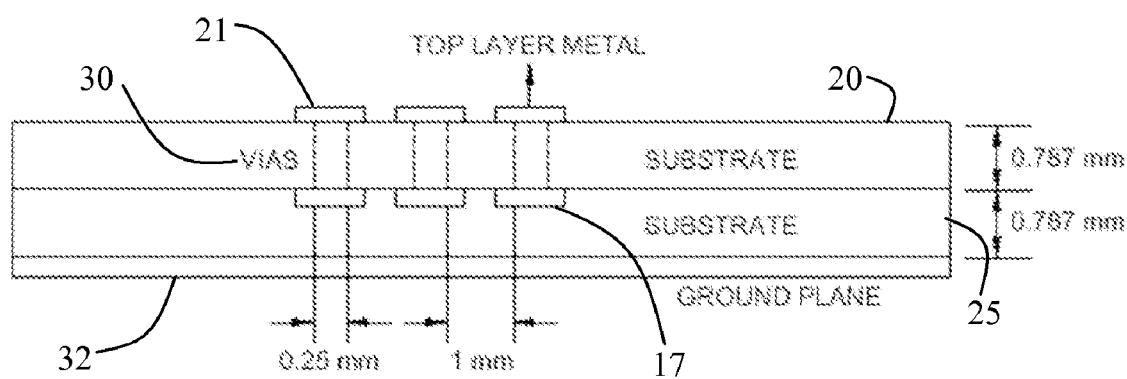
FIG. 2 is a cross sectional diagrammatic view illustrating the embedded toroidal coil of the conductivity sensor in accordance with the present invention.

FIG. 2 illustrates a cross sectional view of the embedded coil in accordance with the present invention.

In a specific embodiment, the coils were designed using 3D EM simulations to get the minimum size possible which could comfortably fit common printed circuit board manufacturer tolerance limits. A variety of coils dimensions and configurations are within the scope of the present invention. The illustrated toroidal coils, in terms of number of turns, size and geometry are exemplary in nature and are not intended to limit the scope of the present invention.

In an additional embodiment, the insulated coil pair is held in close proximity inside the fluid to be measured utilizing nylon screws and connectivity to the radio frequency sensing circuitry is provided through coaxial cables.

Figure 3:
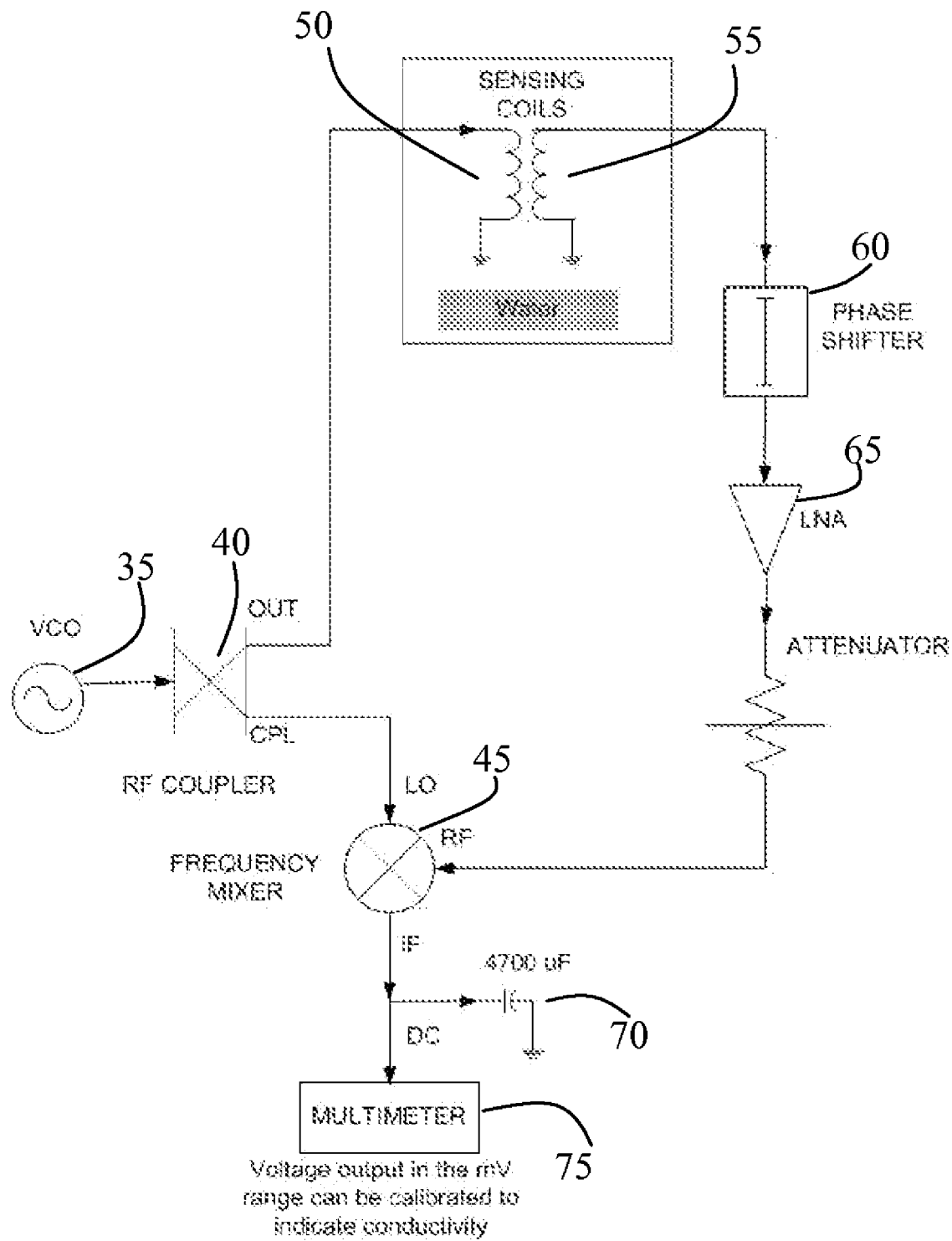
FIG. 3 is a diagrammatic view of a schematic of the conductivity sensor in accordance with the present invention.

FIG. 3 provides a schematic diagram of the toroidal coil and the sensing mechanism of the present invention. In a specific embodiment, the phase detection circuit of the sensing mechanism includes a voltage controlled oscillator (VCO) 35 tuned to provide a signal frequency of 426 MHz at a power of 10 dBm. The signal from the VCO is then split into two parts by a 6.3 dB coupler 40. The coupled signal is fed to a local oscillator (LO) port of a frequency mixer 45 to be used as the reference signal. The output from the direct port of the coupler is fed to one of the sensing coils 50 as the input. The coupled signal that comes out of the second coil 55 is highly attenuated in the sea water and is therefore amplified 65 prior to entering the mixer 45 to bring its power level to that of the LO signal. The mixer 45 now has inputs from the LO and RF at the same frequency and thus outputs the sum and difference of these two signals at the intermediate frequency (IF) port. This output is ideally a DC signal, proportional to the phase difference between the RF and the LO signals. In practical cases, the IF output consists of frequency components arising from harmonics. These harmonics are then filtered out by passing the signal through a high-value bypass capacitor 70. A phase shifter 60 is introduced to modify the output voltage for calibration and initial adjustment purposes.

In a particular embodiment, the sensor electronics which form the phase detection circuit are soldered onto microstrip transmission lines designed for 50Ω impedance on a 59-mil thick FR4 board.

Figure 4:
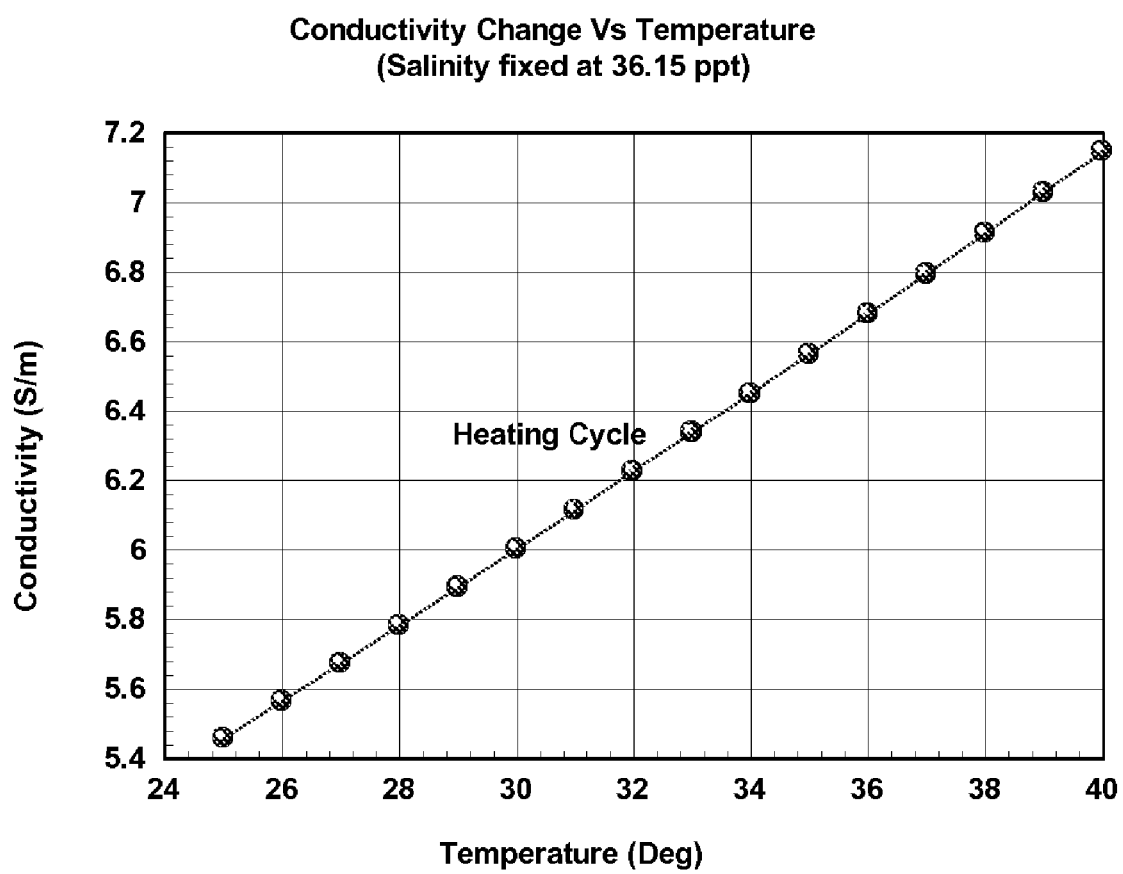
FIG. 4 is a graphical illustration of the calculated variation of conductivity with temperature for a sea water sample of a fixed salinity of 36.15 ppt.

It is known that the conductivity and the permittivity of sea water changes with temperature. In an additional embodiment, a thermistor is mounted on the insulated toroidal coils to monitor the water temperature. Sea water is a dielectric medium with a typical dielectric constant of about 80. The change in conductivity can be quantified using the well known Weyl's equation. The calculated variation of conductivity with temperature for a sea water sample of a fixed salinity of 36.15 ppt is shown in FIG. 4. This variation in conductivity and permittivity, and thus the propagation constant, is the underlying principle of the radio frequency (RF) phase detection method in accordance with the present invention. The RF signal that couples from one coil to another in the sensor undergoes a change in its phase as it couples through the medium to the second coil. This phase change is proportional to the change in the complex permittivity, which in turn is related to the conductivity of the sea water. This phase change is detected by the phase detection circuit described in the previous section. The output voltage of the phase detector is given by $V=A*\cos(\Theta+\Theta_{RT})$, where V is the DC output voltage read by the multimeter, $\Theta$ is the phase shift due to the conductivity change and $\Theta_{RT}$ the phase value corresponding to room temperature. The parameter 'A' adjusts the voltage amplitude and is also temperature dependent.

As shown in FIG. 4, the change in conductivity with temperature is not a perfectly linear relationship. It can be averaged out to an approximate value for a fixed value of salinity. For example, the change in salinity for a solution of 36.15 ppt salinity is shown in 5. In this case the conductivity change can be averaged at about 0.115 S/m per deg change in temperature.

In an exemplary embodiment, the sensor in accordance with the present invention was tested in two sea water samples of different salinities of 36.15 ppt and 10.007 ppt. The sea water was taken in a glass beaker with a stirrer and placed on a digital hot plate. The solution was continuously stirred as it was heated to ensure uniform temperature distribution in the beaker. Output voltage readings were taken for every one degree rise in temperature starting from 25 deg up to 40 degrees. The change in the magnitude of the measured output voltage per degree change in temperature was proportional to the change in conductivity of the sea water. The initial value and the polarity of the output voltage can be controlled by adjusting the phase shift provided by the phase shifter. The intentionally induced phase shift is also used to maximize the sensitivity of the sensor.

Figure 5:
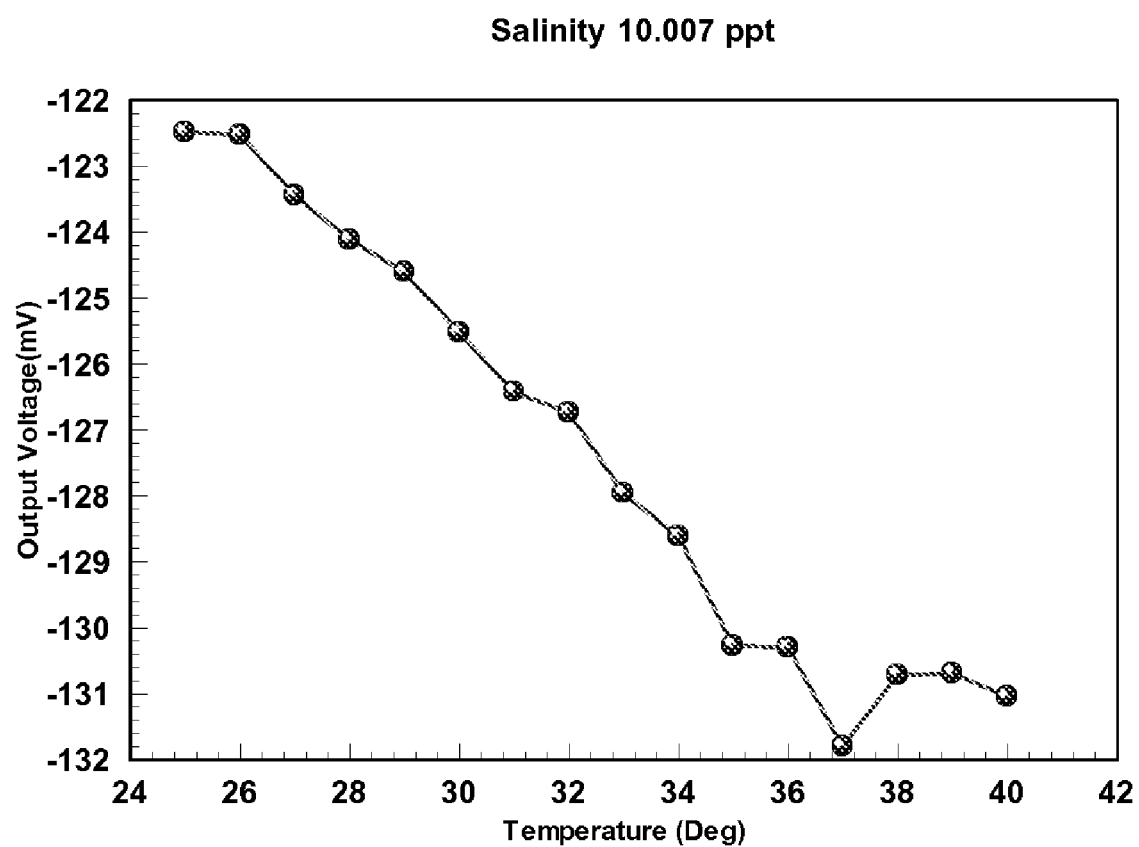
FIG. 5 a graphical illustration of the output voltage response of the sensor in an experimental solution of salinity 10.007 ppt.

The output voltage response of the sensor in an experimental solution of salinity 10.007 ppt is shown in FIG. 5. The output voltage recorded at each temperature setting varied from about −121 mV to −131 mV, providing a range of 10 mV across the temperature span under consideration. The calculated conductivity values based on Weyl's equations ranges from 5 S/m at 25 deg to 7 S/m at 40 deg. This translates to a sensitivity of about 5 mV per 1 S/m change in conductivity measured by the sensor.

Figure 6:
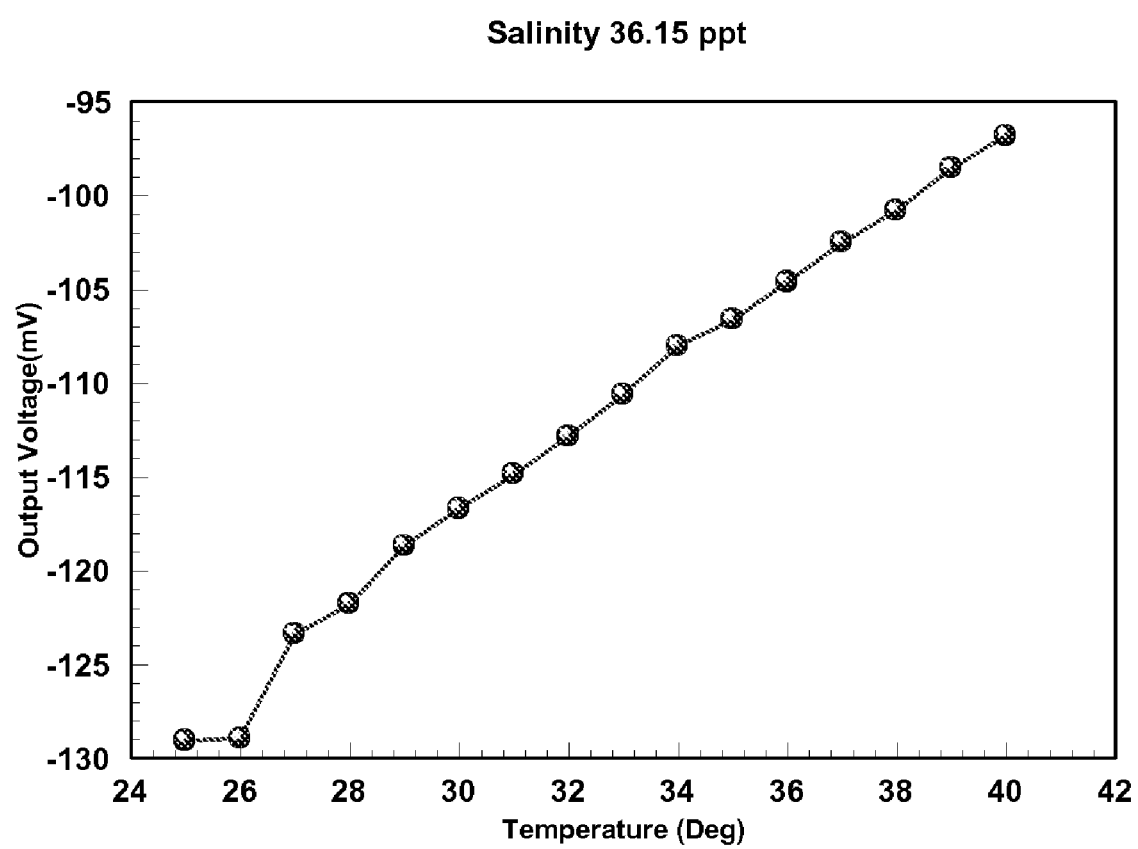
FIG. 6 is a graphical illustration of the output voltage response of the sensor in an experimental solution of salinity of 36.15 ppt.

FIG. 6 illustrates the output voltage response of a sea water sample of 36.15 ppt salinity. The voltage variation is about −95 to −130 mV, which is about 35 mV across the same temperature range. This shows that the as the salinity increases, the rate of conductivity change also increases.

Several different designs were evaluated with different number of turns, turn lengths and core geometry as indicated in the table of FIG. 7. The number of turns was varied as 8, 12 and 20 to vary the inductance. The turn length was also varied to obtain different inductance values for a fixed number of turns. The variations due to core shape were examined using square and circular coils.

Figure 8:
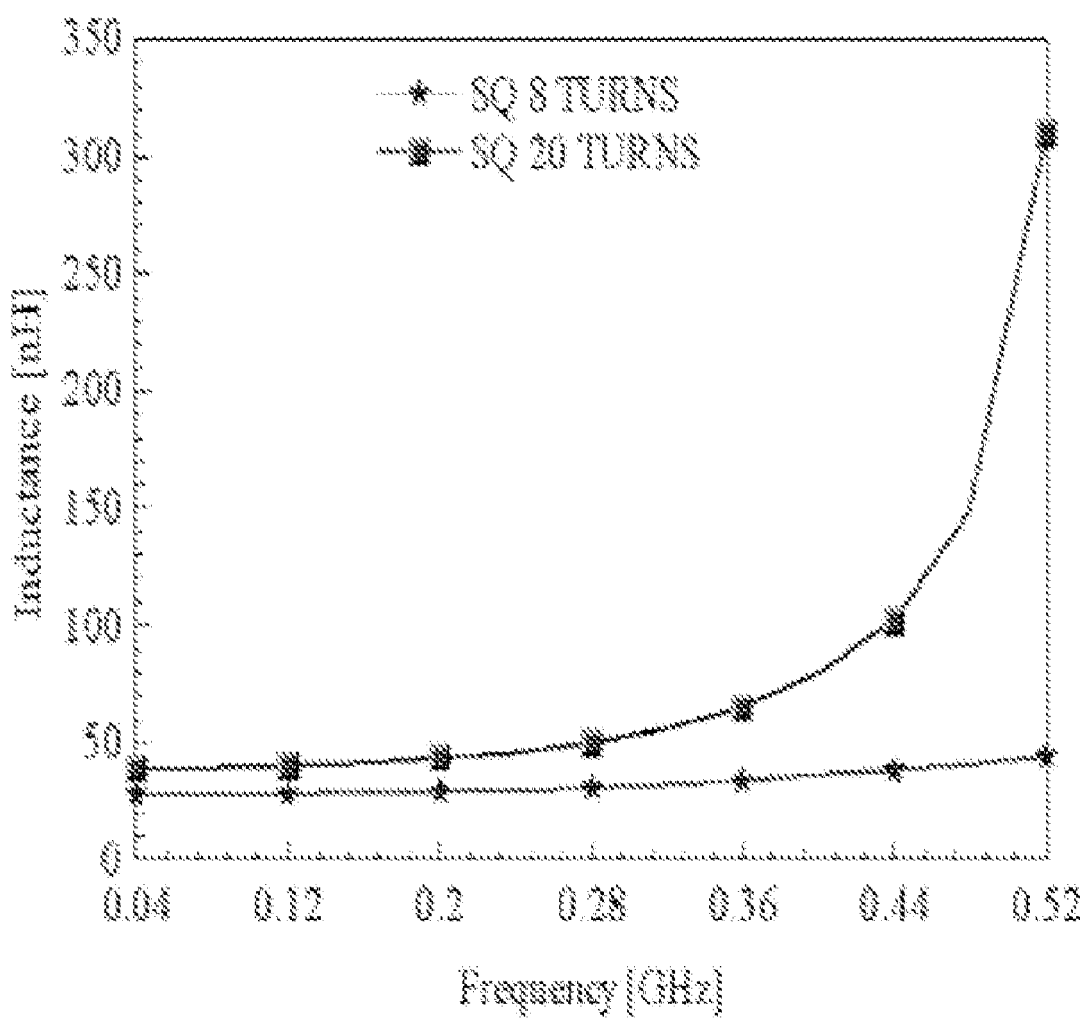
FIG. 8 is a graphical illustration of the low frequency inductance for the square core 8 and 20 turn models in accordance with the present invention.

S-parameter measurements were made on the 1-port configurations from 50 MHz to 1.5 GHz. A vector network analyzer and a probe station fitted with microwave probes was used for the measurements. The inductance, Q factor, and series resistance of the coils were measured. An off-load Short, Open, Load calibration was performed using a standard calibration substrate before the measurements were made on the FR4 substrate. Sample data provided in FIG. 8 shows the low frequency inductance for the square core 8 and 20 turn models. The self-resonant frequency is affected by the capacitance between the turns, which is dependent in part on the distance between the turns.

Figure 9:
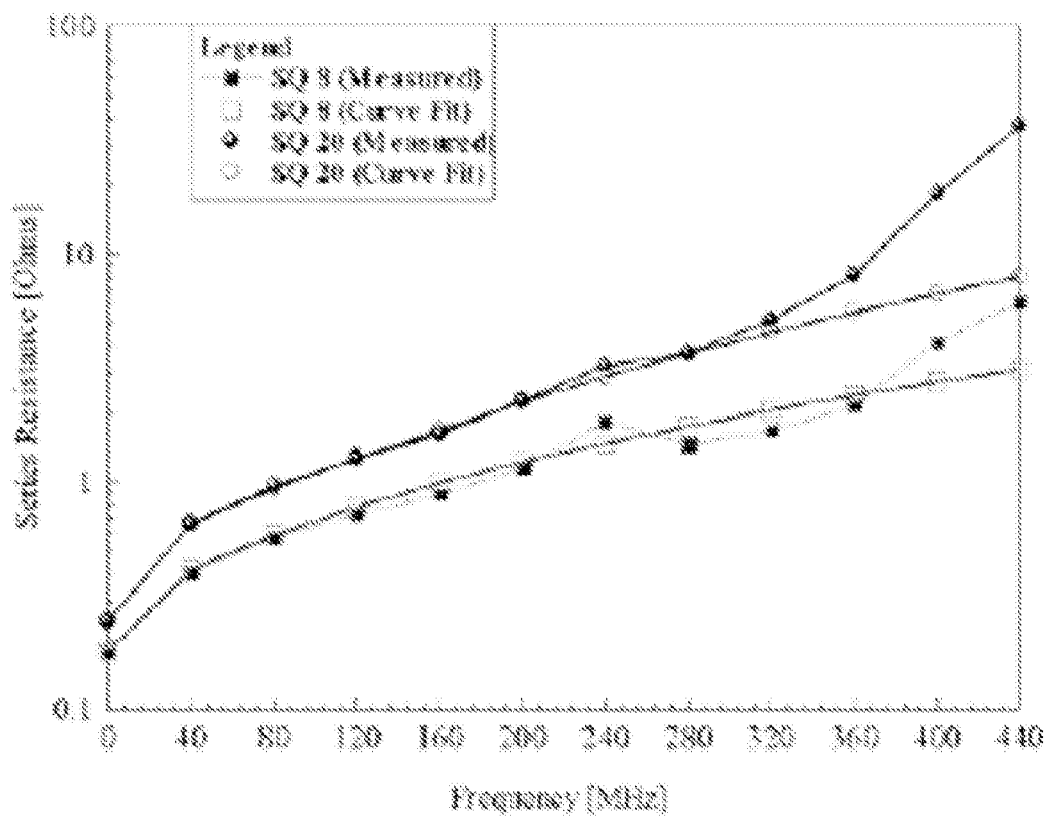
FIG. 9 is a graphical illustration of a comparison plot of the ESR and measured series resistance values.

Effective Series Resistance (ESR) is the frequency dependent AC resistance acting in series with the inductance. It can be represented as:

$$ESR = a + b*\mathrm{Sqrt}(\mathrm{freq}) + c*\mathrm{freq}\hat{\ }d$$

Where a is the DC resistance of the coil and b-d are constants. The values of the constants are determined by curve-fitting against the measured resistance values. A comparison plot of ESR curve fits and measured series resistance is shown in FIG. 9. The accuracy of the curve fit reduces at higher frequencies, due to the inability to capture the radiation effects that cause considerable losses at higher frequencies.

Figure 10:
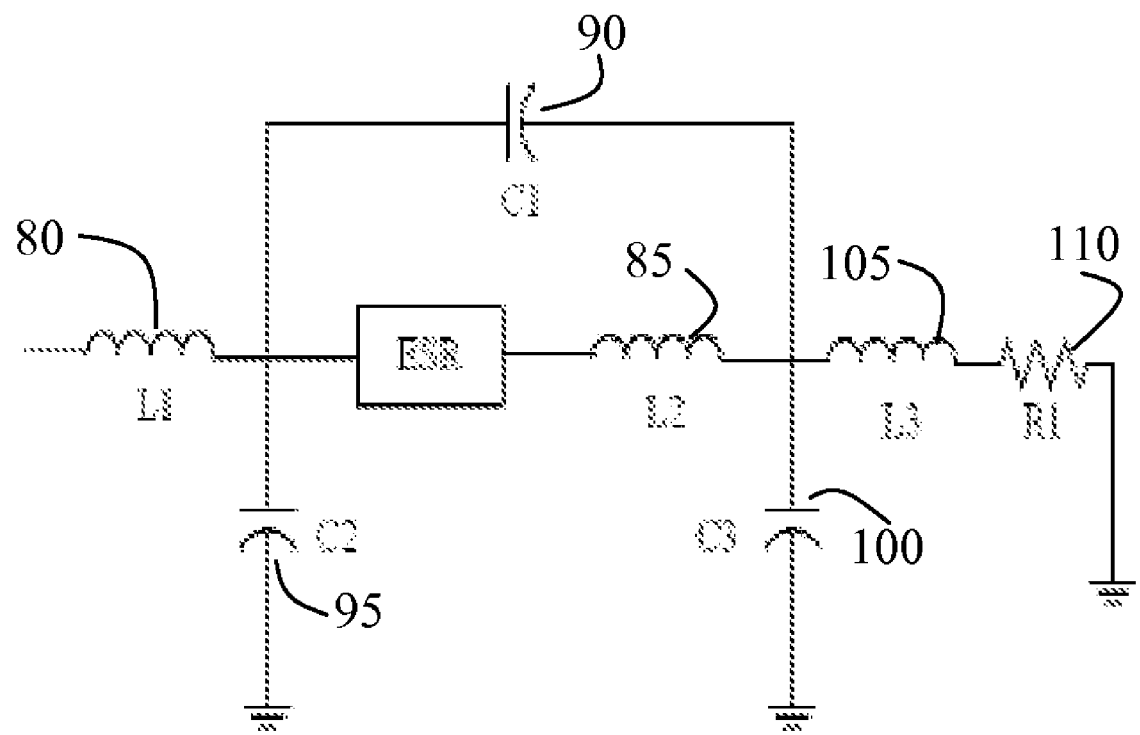
FIG. 10 is a schematic diagram illustrating an equivalent circuit model of an embodiment of the present invention.

The measured S-parameter and ESR data were used to optimize the parameters in a lumped element equivalent circuit model. The circuit model topology for the 1-port configuration is shown in FIG. 10. Here L1 80 represents the inductance of the 50 ohm feed line between the measurement reference plane and the coil input. L2 85 is the effective coil inductance. The capacitance C1 90 represents the capacitance between turns of the coil, while C2 95 and C3 100 represent the pad capacitance and the capacitance between the coil and the group, respectively. The inductance L3 105 and the series resistor R1 110 represents a via to ground at the terminated port of the coil. The optimized circuit element values are summarized in the table of FIG. 11. The values of L1, L3 and R1 are identical for all square coils since the feed line and output via to ground have the same physical dimensions; the same holds true for all circular coils. There is a difference in L3 and R1 between the square and circular designs, owing to a difference in the diameter of the via. The CIR 3MM design shows a high value for C3 due to the relatively large area of the coil; the turn length in circular coils is measured in the radial direction, which means shorter turns are broader thus increasing the effective metal area.

Figure 12:
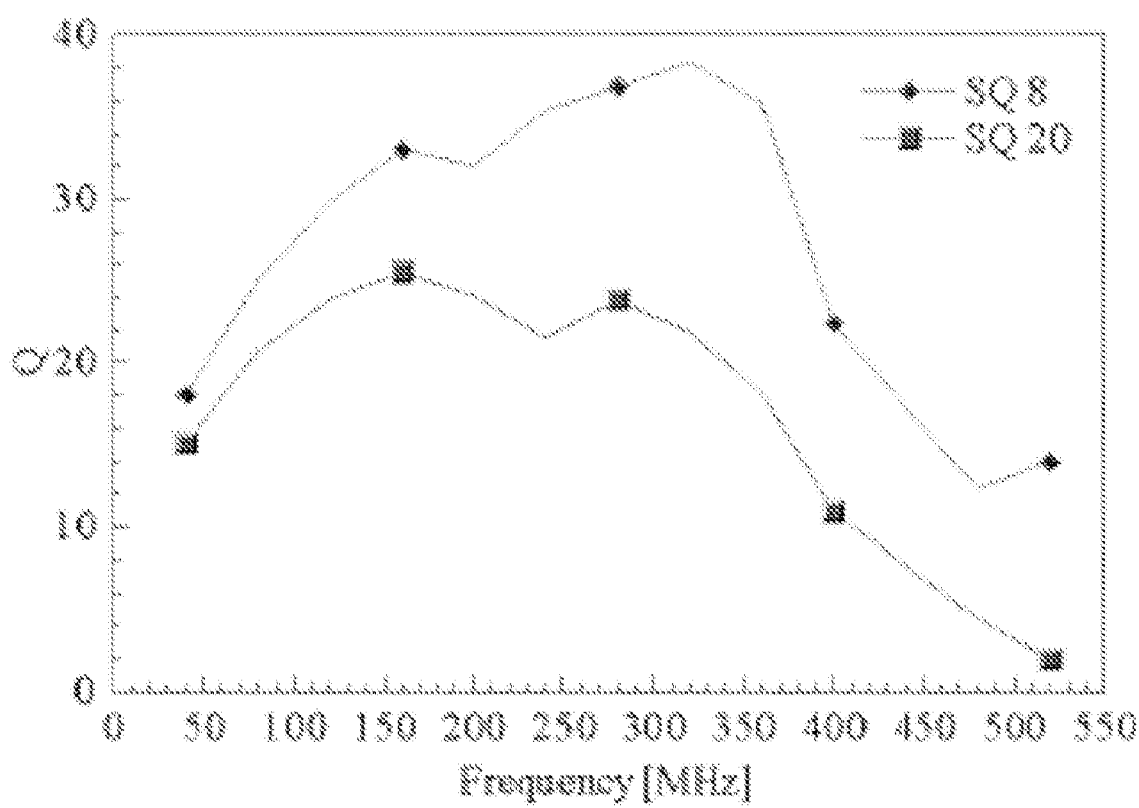
FIG. 12 is a graphical illustration of the Q-factor of the square core coils.

The frequency-dependent Q-factors for the 8 and 20-turn square toroid designs are shown in FIG. 12, with a tabulation of peak Q-factors for all designs given in the table of FIG. 13. The Q values are relatively lower than comparable surface mount inductors, primarily due to the dissipative loss of the FR4 core.

Figure 14:
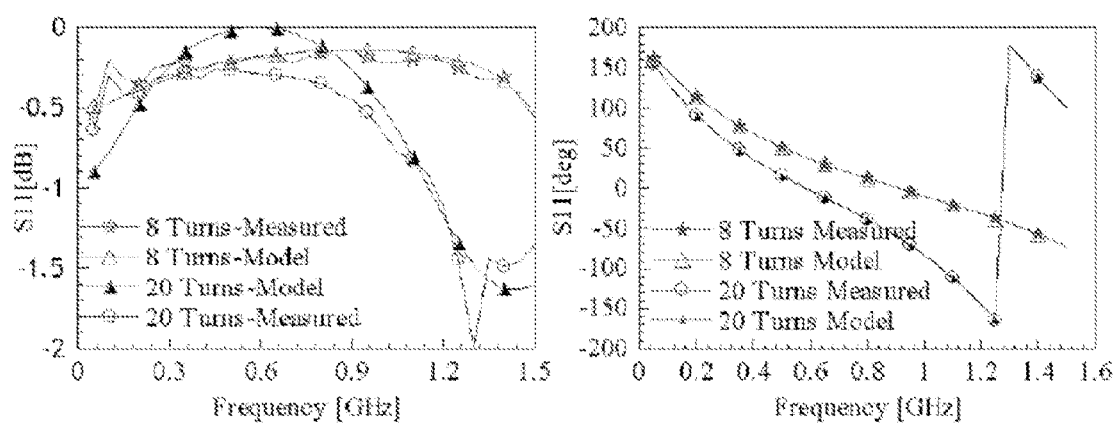
FIG. 14 is a graphical illustration of a comparison of measured and modeled S-parameter data for several toroidal designs.

The plots in FIG. 14 show a comparison between the measured and modeled S-parameter data for the square core 8 and 20 turns designs. The designs were arbitrarily selected for comparison. A close match is observed both in the S11 (dB) and the phase values. The near perfect match validates the component values of the model tabulated in the table of FIG. 11.

As such, for circuit designs requiring a low profile, the 3-D toroid topology in accordance with the present invention is advantageous and offers greater field confinement than planar spiral designs with comparable manufacturing complexity.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A fluid conductivity sensor embedded in a printed circuit board, the sensor comprising:
a first toroidal coil embedded in a printed circuit board and a second toroidal coil, the first coil positioned in close proximity to the second coil to establish a toroidal inductor having a core of dielectric material; and
a radio frequency phase detection circuit coupled to the toroidal inductor to detect the conductivity of the fluid, the radio frequency phase detection circuit further comprising:
a voltage controlled oscillator tuned to output a radio frequency signal;
a coupler coupled to the voltage controlled oscillator to generate a reference signal and an output signal from the radio frequency signal, the output signal of the coupler received as an input signal to the first toroidal coil;
an amplifier to receive an output signal from the second toroidal coil in response to the input signal to the first toroidal coil; and
a frequency mixer to receive the reference signal from the coupler and the output signal from the second toroidal coil, and to output a phase difference signal representing the difference between the reference signal from the coupler and the output signal from the toroidal coil.

2. The fluid conductivity sensor of claim 1, wherein the first toroidal coil and the second toroidal coil further comprises:
a ground plane layer;
a first dielectric substrate layer positioned adjacent to the ground plane layer;
a first plurality of microstrip conductive elements positioned on the first dielectric substrate layer;
a second dielectric substrate layer positioned to overly the first dielectric substrate layer and the first plurality of conductive elements;
a second plurality of microstrip conductive elements positioned on the second dielectric substrate layer; and
a plurality of vias positioned to provide electric connection between the first plurality of conductive elements and the second plurality of conductive elements to establish a toroidal coil within the substrate layers of the printed circuit board.

3. The fluid conductivity sensor of claim 2, wherein the first dielectric substrate layer is composed of FR4.

4. The fluid conductivity sensor of claim 2, wherein the second dielectric substrate layer is composed of FR4.

5. The fluid conductivity sensor of claim 2, wherein the first conductive elements and the second conductive elements are gold metallized.

6. The fluid conductivity sensor of claim 1, further comprising a thermistor to monitor the temperature of the fluid.

7. The fluid conductivity sensor of claim 1, wherein the radio frequency phase detection circuit further comprises a filter circuit coupled to the output of the frequency mixer.

8. The fluid conductivity sensor of claim 1, wherein the radio frequency phase detection circuit further comprises a phase shifter coupled between the second toroidal coil and the frequency mixer.

9. The fluid conductivity sensor of claim 1, wherein the radio frequency signal from the voltage controlled oscillator has a frequency of about 426 MHz and a power of about 10 dBm.

10. A method for measuring the conductivity of a fluid, the method comprising the steps of:
placing a first toroidal coil embedded in a printed circuit board and a second toroidal coil within a fluid to be measured, the first coil positioned in close proximity to the second coil to establish a toroidal inductor having a core of dielectric material;
establishing a radio frequency signal;
splitting the radio frequency signal to generate a reference signal and an output signal from the radio frequency signal;
providing the output signal as an input signal to the first toroidal coil;
establishing an output signal from the second toroidal coil in response to the input to the first toroidal coil;
amplifying the output signal from the second toroidal coil; and measuring the phase difference between the amplified output signal from the second toroidal coil and the reference signal, the phase difference representative of the conductivity of the fluid.

11. The method of claim 10, further comprising the step of filtering the phase difference signal to remove unwanted harmonics.

12. The method of claim 11, further comprising the step of phase shifting the output signal from the second toroidal coil to modify the output signal for calibration.

13. The method of claim 10, further comprising the step of monitoring the temperature of the fluid.

\* \* \* \* \*

UNITED STATES PATENT AND TRADEMARK OFFICE
CERTIFICATE OF CORRECTION

PATENT NO. : 7,479,864 B2  Page 1 of 1
APPLICATION NO. : 11/425231
DATED : January 20, 2009
INVENTOR(S) : Weller et al.

It is certified that error appears in the above-identified patent and that said Letters Patent is hereby corrected as shown below:

Please amend the Letters Patent as follows:

On title page please delete Item (76) insert Item (75)

--Thomas M. Weller, Lutz, FL (US)
David P. Fries, Petersburg, FL (US)
Saravana P. Natarajan, Tampa, FL (US)--

Add Item (73)

University of South Florida
3802 Spectrum Blvd., Suite 100
Tampa, FL 33612

Signed and Sealed this

Fifteenth Day of June, 2010

David J. Kappos
*Director of the United States Patent and Trademark Office*